United States Patent
Mino et al.

[11] Patent Number: 5,868,827
[45] Date of Patent: Feb. 9, 1999

[54] CHEMICALLY BONDING MATERIAL AND METHOD FOR MANUFACTURING THE SAME

[75] Inventors: Norihisa Mino; Kazufumi Ogawa, both of Nara; Yasuo Takebe, Kyoto; Tadashi Otake, Osaka, all of Japan

[73] Assignee: Matsushita Electric Industrial Co., Ltd., Osaka, Japan

[21] Appl. No.: 988,645

[22] Filed: Dec. 11, 1997

[30] Foreign Application Priority Data

Dec. 16, 1996 [JP] Japan .................................. 8-335927

[51] Int. Cl.$^6$ ..................... C09D 183/04; C09D 183/06; C09D 183/07
[52] U.S. Cl. ................. 106/287.13; 106/287.14; 106/287.16; 106/287.19
[58] Field of Search ........................ 106/287.13, 287.14, 106/287.16, 287.19

[56] References Cited

U.S. PATENT DOCUMENTS

| | | |
|---|---|---|
| 5,001,110 | 3/1991 | Nonaka et al. ............................. 505/1 |
| 5,275,849 | 1/1994 | Castelli et al. . |
| 5,433,941 | 7/1995 | Patel .......................................... 424/50 |
| 5,505,997 | 4/1996 | Strong et al. . |

FOREIGN PATENT DOCUMENTS

| | | |
|---|---|---|
| 4-256466 | 9/1992 | Japan . |
| 8-267640 | 10/1996 | Japan . |

*Primary Examiner*—David Brunsman
*Attorney, Agent, or Firm*—Merchant, Gould, Smith, Edell, Welter & Schmidt, P.A.

[57] ABSTRACT

A method for manufacturing a chemically bonding material comprising the steps of: mixing a compound expressed by a general formula $ABX_n$ (Formula 1), wherein A shows a group including carbon, B indicates Si, Ge, Sn, Ti or Zr, X is a hydrolyzable group and n indicates 1, 2 or 3, and at least one kind of compound not including active hydrogen groups in a dry atmosphere having a water vapor density of 0.0076 kg/m$^3$ or less; and storing the same in a dry atmosphere having a water vapor density of 0.0076 kg/m$^3$ or less. A coating solution including compounds that are easily hydrolyzed is stored in a dry state so that the material is not deactivated before reacting with a substrate.

24 Claims, No Drawings

CHEMICALLY BONDING MATERIAL AND METHOD FOR MANUFACTURING THE SAME

FIELD OF THE INVENTION

The present invention relates to a chemically bonding material that forms a thin coating film on a surface of glass, plastic, metal or the like and to a method for manufacturing the same.

BACKGROUND OF THE INVENTION

It is well known to process the surface of a substrate such as glass by using silane-based, germanium-based, tin-based, titanium-based or zirconium-based molecules, for example, in the case of manufacturing a glass fiber reinforced plastic (FRP) by improving the adhesiveness between the glass fibers and the plastics.

The conventional methods will be explained employing examples using silane-based molecules as follows. The conventional methods using germanium-based, tin-based, titanium-based or zirconium-based molecules may use the same method as in the example using silane-based molecules explained below.

Silane-based molecules used in a first conventional example are chlorosilane-based molecules. Other halosilane molecules such as bromine silane-based molecules or the like have the same functions as chlorosilane-based molecules. A solution is prepared by dissolving in alcohol silane-based molecules having monochlorosilane groups, dichlorosilane groups or trichlorosilane groups as a material for forming a coating film. A method of dipping a substrate into the solution, a method of applying the solution to a substrate, a method of spraying the solution on a substrate or the like is used as a method for forming a coating film on a substrate using the solution. A coating film made up of chlorosilane-based molecules is formed using any one of such methods, although there are differences in thickness and in uniformity of the film in each method.

Next, a second conventional example will be explained as follows. Molecules used here are alkoxysilane-based molecules. Isocyanate-based molecules have the same functions as the alkoxysilane-based molecules. A solution is prepared by dissolving silane-based molecules having monoalkoxysilane groups, dialkoxysilane groups or trialkoxysilane groups as a material for forming a coating film in hydrocarbon molecules. A method of dipping a substrate into the solution, a method of applying the solution to a substrate, a method of spraying the solution on a substrate or the like is used as a method for forming a coating film on a substrate using the solution. A coating film made up of alkoxysilane-based molecules is formed using any one of such methods, although there are differences in thickness and in uniformity of the film in each method. Then, the substrate on which a film has been formed is fired, wherein a temperature of 100° C. and a time period of one hour usually are employed as standard conditions. As a result, a siloxane bond is formed by a dehydration reaction, a dealcoholization reaction or the like between alkoxy groups of the alkoxysilane-based molecules and hydroxyl groups of the alkoxysilane-based molecules already hydrolyzed, between alkoxy groups of the alkoxysilane-based molecules, between hydroxyl groups of the alkoxysilane-based molecules already hydrolyzed, between hydroxyl groups on the surface of the substrate and alkoxy groups of the alkoxysilane-based molecules, or between hydroxyl groups on the surface of the substrate and hydroxyl groups of the alkoxysilane-based molecules already hydrolyzed, thus forming a coating film.

As a third conventional example, a solution is prepared by dissolving chlorosilane-based molecules in a silicone oil. The solution prepared here is applied to a substrate by using the same method as in the first example, and thus forming a coating film.

However, in the case of using the method for forming a coating film in the first conventional example mentioned above, the chlorosilane groups of the chlorosilane-based molecules react with the alcohol in which the chlorosilane groups dissolve, and alkoxysilane groups are formed. The alkoxysilane groups are changed to silane groups having high reactivity, and the chlorosilane-based molecules, alkoxy-based molecules changed from the chlorosilane-based molecules, silanol-based molecules changed further from the alkoxy-based molecules and the like react with each other. As a result, a thick coating film having a non-uniform thickness is formed. Furthermore, a tight chemically bonded film should be inherently formed by the reaction between hydroxyl groups on the surface of the substrate such as glass or the like and the chlorosilane groups or the alkoxy groups. However, the film formed here is not tightly bonded to the substrate, since the number of reactive chlorosilane groups, alkoxysilane groups and silanol groups which are included in the material molecules is overwhelmingly more than the number of the hydroxyl groups exposed on the surface of the substrate, and the great majority of the molecules therefore react with each other. Similarly, in the second conventional example, a coating film similar to that of the first conventional example is formed, since a reaction occurs between the alkoxysilane-based molecules and the silanol-based molecules changed from the alkoxysilane-based molecules. In the third conventional example, the chlorosilane-based molecules are not changed to silanol-based molecules, since the solution is composed of silicone oil and oils, which does not include water. However, the atmosphere in the dissolving process is not a dry atmosphere, so that a little water content comes to be included during the dissolving process. The water molecules are changed to silanol-based molecules by reacting gradually with the chlorosilane-based molecules, thus forming an oligomer. As a result, as a storage time of the material becomes longer, a coating film formed becomes similar to that of the first and second conventional examples.

In the first, second and third conventional examples, the atmosphere is not controlled so as to be a dry atmosphere during the production of a chemically bonding material, the preparation of the material into a coating solution composition and the storage of the composition. Therefore, the method according to the first, second and third conventional examples mentioned above is disadvantageous in that the silane-based molecules are deactivated and do not react with the surface of a substrate such as glass or the like.

SUMMARY OF THE INVENTION

In order to solve the problems mentioned above in the prior art, it is an object of the present invention to provide a method improved so as to enable a chemically bonding material for forming a thin coating film whose thickness is less than a micrometer and is uniform to be produced without being deactivated, to be prepared into a coating solution composition and to be stored.

A method for manufacturing a chemically bonding material and a chemically bonding material according to the present invention are characterized in that a compound expressed by the following general formula 1 (Formula 1), wherein A shows a group including carbon, B indicates Si, Ge, Sn, Ti or Zr, X is a hydrolyzable group and n indicates 1, 2 or 3, and at least one kind of compound not including active hydrogen groups are mixed, kneaded or dissolved in a dry atmosphere having a water vapor density of 0.0076 kg/m$^3$ or less.

(Formula 1)

$$ABX_n$$

In manufacturing a chemically bonding material composed of molecules expressed by Formula 1 and at least two kinds of molecules not including active hydrogen groups, the at least two kinds of molecules not including active hydrogen groups are pre-mixed, pre-kneaded or pre-dissolved in an atmosphere having a water vapor density of 0.011 kg/m$^3$ or less. Then, a mixture, a kneaded material or a dissolved material composed of at least the two kinds of molecules not including active hydrogen groups and the molecules expressed by Formula 1 is prepared by, for example, mixing, kneading or dissolving in an atmosphere having a water vapor density of 0.0076 kg/m$^3$ or less, In the situation mentioned above, the molecules not including active hydrogen groups are preferably non proton-based molecules, hydrocarbon molecules, siloxane molecules, carbon tetrachloride, chloroform or dichloroethane.

The molecules not including active hydrogen groups are preferably stored in an atmosphere having a water vapor density of 0.0076 kg/m$^3$ or less before being mixed with, kneaded with or dissolved in the molecules expressed by Formula 1 in an atmosphere having a water vapor density of 0.0076 kg/m$^3$ or less.

Furthermore, the molecules expressed by Formula 1 are preferably stored in an atmosphere having a water vapor density of 0.0076 kg/m$^3$ or less before being mixed with, kneaded with or dissolved in the molecules not including active hydrogen groups in an atmosphere having a water vapor density of 0.0076 kg/m$^3$ or less.

Materials further added other than the molecules expressed by Formula 1 and the molecules not including active hydrogen groups which are included in the chemically bonding material are also preferably stored in an atmosphere having a water vapor density of 0.0076 kg/m$^3$ or less before being mixed, kneaded or dissolved in an atmosphere having a water vapor density of 0.0076 kg/m$^3$ or less.

Moreover, the material further added is preferably an inorganic substance, an inorganic oxide or a mineral salt. The material further added may be any one of, for example, a silica gel, calcium sulfate anhydride, calcium oxide, magnesium oxide or the like, which is generally used for a desiccating agent or a dehumidifying agent.

DESCRIPTION OF THE PREFERRED EMBODIMENTS

The present invention will be explained in more detail as follows. According to the present invention, in the process of mixing, kneading or dissolving at least molecules expressed by Formula 1 and molecules not including active hydrogen groups, the water content included in the material that has been mixed, kneaded or dissolved can be restrained by controlling the water vapor density, based on the measurement by a hygrometer, so as to be 0.0076 kg/m$^3$ or less. As a result, the performance of a coating film manufactured using the material can be maintained.

The molecules expressed by Formula 1 and the molecules not including active hydrogen groups both are preferably stored in an atmosphere having a water vapor density of 0.0076 kg/m$^3$ or less before being mixed, kneaded or dissolved together.

When there are molecules added other than the two kinds of molecules mentioned above, the molecules added are preferably stored also in an atmosphere having a water vapor density of 0.0076 kg/m$^3$ or less.

Furthermore, in measuring humidity using a hygrometer, the lower limit of humidity cannot be provided, since the lower limit is changed according to the storage condition (high temperature storage, low temperature storage) and the length of the storage time of the chemically bonding material of the present invention. Generally, a material constitution that is endurable against high temperature storage and long term storage can be obtained as the value of the humidity measured using a hygrometer approaches 0%.

However, in the case of preparing a chemically bonding material in an atmosphere having a water vapor density over 0.0076 kg/m$^3$, the material deteriorates between the time when the material is manufactured and the time when the material is actually used by a user, excepting the case of use right after the preparation of the material, since the reaction between the materials is accelerated.

According to the present invention, a molecular film having a thickness in the range from about 0.1 nm to about 1 μm can be formed on a substrate by forming siloxane bonds between the substrate and silane-based compounds.

It is preferable that the silane-based compound be a compound comprising an alkyl group or a fluoroalkyl group. A specific example of the compound comprising a fluoroalkyl group includes a fluoroalkylsilane compound expressed by a general formula $C_nF_{2n+1}(CH_2)_2SiCl_3$ (n=a positive integer of 1 to 30), such as heptadecafluoro1,1,2,2,tetrahydrodecyltrichlorosilane or the like.

As a solvent for dissolving the chlorosilane-based compound, any solvent can be used, as long as it does not contain active hydrogen atoms that react with the chlorosilane-based compound. For example, a hydrocarbon-based solvent, a hydrocarbon halide-based solvent, an alkylsiloxane-based solvent, or a silicone oil-based solvent can be used for the fluoroalkylsilane compound. Specific examples of the hydrocarbon-based solvent include a solvent of oils expressed by a general formula $C_nH_{2n+2}$ (n=a positive integer) such as a turpentine oil or the like, or expressed by a general formula $C_nH_{2n}$. Specific examples of the hydrocarbon halide-based solvent include a solvent expressed by a general formula $C_nH_{2n-m+2}X_m$ (n=a positive integer, m=a positive integer, and X=halogen) such as octadecafluorooctane or the like. Specific examples of the alkylsiloxane-based solvent include a linear silicone solvent expressed by a general formula $R^1(R^2R^3SiO)_nR^4$ (n=a positive integer, $R^1$, $R^2$, $R^3$, and $R^4$=alkyl groups) such as hexamethyldisiloxane or the like, or a cyclic silicone solvent expressed by a general formula $(R^1R^2SiO)_n$ (n=a positive integer, $R^1$ and $R^2$=alkyl groups) such as octamethylsiloxane, or a mixture thereof.

Examples of a chemically bonding material that can be used in the present invention are listed below:

  (1)

  (2)

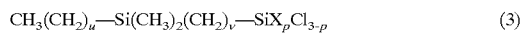  (3)

  (4)

(where p is an integer of 0 to 2, r is an integer of 1 to 25, s is an integer of 0 to 12, t is an integer of 1 to 20, u is an integer of 0 to 12, v is an integer of 1 to 20, and w is an integer of 1 to 25. X is hydrogen, an alkyl group, an alkoxyl group, a fluorine containing alkyl group, or a fluorine containing alkoxyl group.)

Furthermore, specific examples of the bonding material are the following compounds:

$$CH_3CH_2O(CH_2)_{15}SiCl_3 \quad (5)$$

$$CH_3(CH_2)_2Si(CH_3)_2(CH_2)_{15}SiCl_3 \quad (6)$$

$$CH_3(CH_2)_6Si(CH_3)_2(CH_2)_9SiCl_3 \quad (7)$$

$$CH_3COO(CH_2)_{15}SiCl_3 \quad (8)$$

$$CF_3(CF_2)_7-(CH_2)_2-SiCl_3 \quad (9)$$

$$CF_3(CF_2)_5-(CH_2)_2-SiCl_3 \quad (10)$$

$$CF_3(CF_2)_7-C_6H_4-SiCl_3 \quad (11)$$

Furthermore, instead of the chlorosilane-based chemically bonding material as described above, an isocyanate-based chemically bonding material obtained by substituting all of the chlorosilyl groups with isocyanate groups can be used. Examples thereof are as follows:

$$CH_3-(CH_2)_r SiX_p(NCO)_{3-p} \quad (12)$$

$$CF_3-(CH_2)_r SiX_p(NCO)_{3-p} \quad (13)$$

$$CH_3(CH_2)_s O(CH_2)_t SiX_p(NCO)_{3-p} \quad (14)$$

$$CH_3(CH_2)_u-Si(CH_3)_2(CH_2)_v-SiX_p(NCO)_{3-p} \quad (15)$$

$$CF_3COO(CH_2)_w SiX_p(NCO)_{3-p} \quad (16)$$

(where, p, r, s, t, u, v, w and X are the same as above.)

Instead of the above-mentioned bonding materials, the bonding material compounds specifically listed below can be used.

$$CH_3CH_2O(CH_2)_{15}Si(NCO)_3 \quad (17)$$

$$CH_3(CH_2)_2Si(CH_3)_2(CH_2)_{15}Si(NCO)_3 \quad (18)$$

$$CH_3(CH_2)_6Si(CH_3)_2(CH_2)_9Si(NCO)_3 \quad (19)$$

$$CH_3COO(CH_2)_{15}Si(NCO)_3 \quad (20)$$

$$CF_3(CF_2)_7-(CH_2)_2-Si(NCO)_3 \quad (21)$$

$$CF_3(CF_2)_5-(CH_2)_2-Si(NCO)_3 \quad (22)$$

$$CF_3(CF_2)_7-C_6H_4-Si(NCO)_3 \quad (23)$$

Furthermore, as the chemically bonding material, in general, a substance expressed by a formula $SiX_k(OA)_{4-k}$ (X is the same as above, A is an alkyl group, and k is 0, 1, 2, or 3) can be used. In particular, when a substance expressed by $CF_3-(CF_2)_n-(R)_q-SiX_p(OA)_{3-p}$ (n is a positive integer of 1 or more, preferably an integer of 1 to 22, R is an alkyl group, a vinyl group, an ethynyl group, an aryl group, silicon or substituent containing an oxygen atom, q is 0 or 1, and X, A, and p are the same as above) is used, a film having a more excellent antifouling property can be used. However, it is not limited thereto. Other examples are $CH_3-(CH_2)_r-SiX_p(OA)_{3-p}$ and $CH_3-(CH_2)_s-O-(CH_2)_t-SiX_p(OA)_{3-p}$, $CH_3-(CH_2)_u-Si(CH_3)_2-(CH_2)_v-SiX_p(OA)_{3-p}$, $CF_3COO-(CH_2)_w-SiX_p(OA)_{3-p}$ (where, p, r, s, t, u, v, w, X and A are the same as above.)

Furthermore, more specific examples of the chemically bonding material are as follows:

$$CH_3CH_2O(CH_2)_{15}Si(OCH_3)_3 \quad (24)$$

$$CF_3CH_2O(CH_2)_{15}Si(OCH_3)_3 \quad (25)$$

$$CH_3(CH_2)_2Si(CH_3)_2(CH_2)_{15}Si(OCH_3)_3 \quad (26)$$

$$CH_3(CH_2)_6Si(CH_3)_2(CH_2)_9Si(OCH_3)_3 \quad (27)$$

$$CH_3COO(CH_2)_{15}Si(OCH_3)_3 \quad (28)$$

$$CF_3(CF_2)_5(CH_2)_2Si(OCH_3)_3 \quad (29)$$

$$CF_3(CF_2)_7-C_6H_4-Si(OCH_3)_3 \quad (30)$$

$$CH_3CH_2O(CH_2)_{15}Si(OC_2H_5)_3 \quad (31)$$

$$CH_3(CH_2)_2Si(CH_3)_2(CH_2)_{15}Si(OC_2H_5)_3 \quad (32)$$

$$CH_3(CH_2)_6Si(CH_3)_2(CH_2)_9Si(OC_2H_5)_3 \quad (33)$$

$$CF_3(CH_2)_6Si(CH_3)_2(CH_2)_9Si(OC_2H_5)_3 \quad (34)$$

$$CH_3COO(CH_2)_{15}Si(OC_2H_5)_3 \quad (35)$$

$$CF_3COO(CH_2)_{15}Si(OC_2H_5)_3 \quad (36)$$

$$CF_3COO(CH_2)_{15}Si(OCH_3)_3 \quad (37)$$

$$CF_3(CF_2)_9(CH_2)_2Si(OC_2H_5)_3 \quad (38)$$

$$CF_3(CF_2)_7(CH_2)_2Si(OC_2H_5)_3 \quad (39)$$

$$CF_3(CF_2)_5(CH_2)_2Si(OC_2H_5)_3 \quad (40)$$

$$CF_3(CF_2)_7C_6H_4Si(OC_2H_5)_3 \quad (41)$$

$$CF_3(CF_2)_9(CH_2)_2Si(OCH_3)_3 \quad (42)$$

$$CF_3(CF_2)_5(CH_2)_2Si(OCH_3)_3 \quad (43)$$

$$CF_3(CF_2)_7(CH_2)_2SiCH_3(OC_2H_5)_2 \quad (44)$$

$$CF_3(CF_2)_7(CH_2)_2SiCH_3(OCH_3)_2 \quad (45)$$

$$CF_3(CF_2)_7(CH_2)_2Si(CH_3)_2OC_2H_5 \quad (46)$$

$$CF_3(CF_2)_7(CH_2)_2Si(CH_3)_2OCH_3 \quad (47)$$

EXAMPLES

A method of manufacturing a chemically bonding material according to the present invention and a chemically bonding material formed by using the same method will be explained in more detail as follows. However, the present invention is not limited to the examples mentioned below.

Example 1

Using a constant humidity bath having a relative humidity based on the measurement by a hygrometer of 30% (a water vapor density of 0.0060 kg/m$^3$) and a temperature of 22° C., 8 g of 1,1,2,2-tetrahydroheptadecafluorooctyltrichlorosilane ($C_8F_{17}(CH_2)_2SiCl_3$) as a chemically bonding material and 40 g of octamethyltetrasiloxane as a solvent were mixed by stirring in an Erlenmeyer flask for 15 minutes, thus preparing a solution. The solution was transferred to a vessel in the constant humidity bath, and then a square glass plate of 30 mm×30 mm was immediately dipped into the solution in the vessel for 30 minutes. As a next step, the solution was put into two glass tubes in the constant humidity bath, and each of the glass tubes was closed with a cover made of plastic. One of the two glass tubes was left in a constant temperature bath maintaining the temperature at 70° C. for five days and the other glass tube was left in a constant temperature bath maintaining the temperature at 100° C. for five days. Then, as in the operation mentioned above, a solution left in a constant humidity bath having a relative humidity of 30% (a water vapor density of 0.0060 kg/m$^3$) and a temperature of 22° C. was put into a vessel, and a square glass plate of 30 mm×30 mm was dipped into the solution for 30 minutes. A dehydrochlorination reaction occurred due to the presence of hydroxyl groups (—OH) on the surface of the glass plate. As a result, a coating film made of 1,1,2,2-tetrahydroheptadecafluorooctyltrichlorosilane was formed (Formula 2). Next, the glass plate was taken out from the solution and the solution remaining on the surface of the glass plate was blown away. When the glass plate was put in the air, hydrolysis and dehydration reactions proceeded as shown in the following Formulas 3 and 4 due to the reaction between water components in the air and the chlorosilane. A water droplet was dropped onto the surface of the three types of glass plates mentioned above, and the angle formed by the water droplet and the surface of the glass plate (a contact angle) was measured. The results are shown in Table 1.

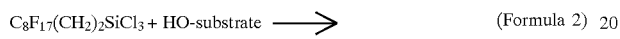
(Formula 2)

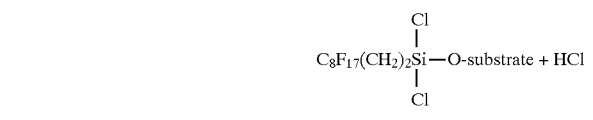
(Formula 3)

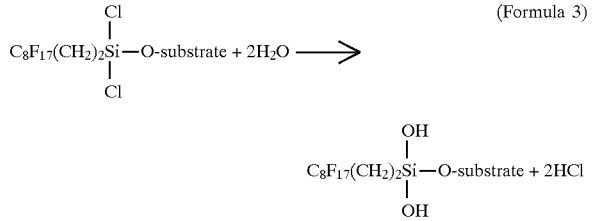
(Formula 4)

Example 2

In a constant temperature bath having a relative humidity based on the measurement by a hygrometer of 48% (a water vapor density of 0.0096 kg/m$^3$) and a temperature of 22° C., 20 g of a hydrocarbon mixture (for example, paraffin (manufactured by Wako Pure Chemical Industries, Ltd.) or paraffin wax (Aldrich Chemical Co. Ink.))having a fusing point at around 70° C. was put into a beaker. The hydrocarbon mixture was heated to 90° C. and melted. Then, 40 g of octamethyltetrasiloxane was further added therein and mixed by stirring for 30 minutes. The solution was transferred into a glove box having a relative humidity based on the measurement by a hygrometer of 5% or less (a water vapor density of 0.0010 kg/m$^3$ or less) (lower than the measuring limit by a hygrometer), and 8 g of 1,1,2,2-tetrahydroheptadecafluorooctyltrichlorosilane was added to the solution and dissolved by stirring for 15 minutes. This solution was put onto a cloth in the same glove box and was immediately applied to a square glass plate of 30 mm×30 mm. Then, extra solution remaining on the glass plate was wiped off with another cloth. As a result, a coating film made of 1,1,2,2-tetrahydroheptadecafluorooctyltrichlorosilane was formed on the surface of the glass plate. Next, the solution was put into two glass tubes in the same glove box mentioned above, and each of the glass tubes was closed with a cover made of plastic. One of the two glass tubes was left in a constant temperature bath maintaining the temperature at 70° C. for five days and another glass tube was left in a constant temperature bath maintaining the temperature at 100° C. for five days. After that, the solution was put onto a cloth and was applied to a glass plate. Then, extra solution remaining on the glass plate was wiped off with another cloth. As a result, a coating film made of 1,1,2,2-tetrahydroheptadecafluorooctyltrichlorosilane was formed on the surface of the glass plate. A water droplet was dropped onto the surface of the three types of glass plates mentioned above, and the contact angles were measured. The results are shown in Table 1.

Comparative Example 1

In a constant humidity bath having a relative humidity based on the measurement by a hygrometer of 69% (a water vapor density of over 0.0137 kg/m$^3$), 8 g of 1,1,2,2-tetrahydroheptadecafluorooctyltrichlorosilane and 40 g of octamethyltetrasiloxane were mixed by stirring in an Erlenmeyer flask for 15 minutes, thus preparing a solution. The solution was transferred to a constant humidity bath having a relative humidity based on the measurement by a hygrometer of 5% or less (a water vapor density of 0.0010 kg/m$^3$ or less) and was put into a vessel. A square glass plate of 30 mm×30 mm was immediately dipped into the solution. As a result, a coating film made of 1,1,2,2-tetrahydroheptadecafluorooctyltrichlorosilane was formed on the surface of the glass plate. Next, the solution was put into two glass tubes in the same constant humidity bath having a relative humidity of 5% or less (a water vapor density of 0.0010 kg/m$^3$ or less), and each of the glass tube was closed with a cover made of plastic. One of the two glass tubes was left in a constant temperature bath maintaining the temperature at 70° C. for five days and another glass tube was left in a constant temperature bath maintaining the temperature at 100° C. for five days. After that, in the same constant humidity bath mentioned above having a relative humidity of 5% or less (a water vapor density of 0.0010 kg/m$^3$ or less), the solution was put into a vessel, and a square glass plate of 30 mm×30 mm was dipped into the solution for 30 minutes. As a result, a coating film made of 1,1,2,2-tetrahydroheptadecafluorooctyltrichlorosilane was formed on the surface of the glass plate. A water droplet was dropped onto the surface of the three types of glass plates mentioned above, and the contact angles were measured. The results are shown in Table 1.

Comparative Example 2

In a constant temperature bath having a relative humidity based on the measurement by a hygrometer of 61% (a water vapor density of over 0.0121 kg/m$^3$), 20 g of a hydrocarbon mixture having a fusing point at around 70° C. was put into a beaker. The hydrocarbon mixture was heated to 90° C. and melted. Then, 40 g of octamethyltetrasiloxane was further added therein and mixed by stirring for 30 minutes. The solution was transferred into a glove box having a relative humidity based on the measurement by a hygrometer of 5% or less (a water vapor density of 0.0010 kg/m$^3$ or less) (lower than the measuring limit by a hygrometer), and 8 g of 1,1,2,2-tetrahydroheptadecafluorooctyltrichlorosilane was added futher to the solution and dissolved by stirring for 15 minutes. This solution was put onto a cloth in the same glove box and was immediately applied to a square glass plate of 30 mm×30 mm. Then, extra solution remaining on the glass plate was wiped off with another cloth. Next, the solution was put into two glass tubes in the same glove box having a relative humidity of 5% or less (a water vapor density of 0.0010 kg/m$^3$ or less), and each of the glass tubes was closed with a cover made of plastic. One of the two glass tubes was left in a constant temperature bath maintaining the temperature at 70° C. for five days and another glass tube was left in a constant temperature bath maintaining the temperature at 100° C. for five days. After that, the solution was put onto a cloth and was applied to a glass plate in the same glove box having a relative humidity of 5% or less (a water vapor density of 0.0010 kg/m$^3$ or less). Then, extra solution remaining on the glass plate was wiped off with another cloth. As a result, a coating film made of 1,1,2,2-tetrahydroheptadecafluorooctyltrichlorosilane was formed on the surface of the glass plate. A water droplet was dropped onto the surface of the three types of glass plates mentioned above, and the contact angles were measured. The results are shown in Table 1.

TABLE 1

| | Contact Angle (°) | | |
|---|---|---|---|
| | Right after Production | After stored at 70° C. | After stored at 100° C. |
| Example 1 | 111 | 110 | 112 |
| Example 2 | 108 | 108 | 108 |
| Comparative Example 1 | 79 | 64 | 52 |
| Comparative Example 2 | 109 | 92 | 80 |

Example 3

In a material in which chlorosilane-based molecules and molecules not having active hydrogen groups are mixed in an environment having high humidity, a hydrogen chloride gas is generated by the reaction between the active hydrogen and the chlorosilane-based molecules that are included in the material. Then, a material in which fine powder of calcium carbonate as a third material was further kneaded with the material was prepared, wherein calcium chloride, carbon dioxide and water molecules were generated due to the reaction between the hydrogen chloride gas and calcium carbonate. The water molecules further react with unreacted chlorosilane-based molecules, so that a hydrogen chloride gas was newly generated. In the case not including active hydrogen groups, neither a hydrogen chloride gas nor carbon dioxide is generated. Therefore, the presence and the amount of the molecules having active hydrogen groups can be known by measuring the amount of carbon dioxide generated. Then, the material in which the three kinds of molecules mentioned above have been mixed was put into a hermetically sealed enclosure, and was stored in a constant temperature bath maintaining the temperature at 70° C. for 40 hours. After that, the amount of carbon dioxide in the hermetically sealed enclosure was measured.

As a pre-kneading process, 4 g of hydrocarbon mixture having a fusing point at around 70° C. was put into a beaker. The solution was heated to 90° C. and dissolved. Then, 8 g of octamethyltetrasiloxane and 8 g of calcium carbonate were further added therein and the solution was kneaded by stirring for 30 minutes. The pre-kneading was carried out under two conditions, i.e. in a constant humidity bath having a relative humidity based on the measurement by a hygrometer of 40% (a water vapor density of 0.0080 kg/m$^3$) and in a constant humidity bath having a relative humidity based on the measurement by a hygrometer of 69% (a water vapor density of over 0.0137 kg/m$^3$). In addition, 1.5 g of 1,1,2,2-tetrahydroheptadecafluorooctyltrichlorosilane and the kneaded material mentioned above were mixed by stirring for 15 minutes. The step of mixing by stirring was carried out under two conditions, i.e. in a glove box having a relative humidity based on the measurement by a hygrometer of 5% or less (a water vapor density of 0.0010 kg/m$^3$ or less) (lower than the measuring limit by a hygrometer) and in a constant humidity bath having a relative humidity based on the measurement by a hygrometer of 69% (a water vapor density of over 0.0137 kg/m$^3$).

The mixed material prepared by the steps mentioned above was put into a container in which a volume expansion can be measured, and was stored in a constant temperature bath having a temperature of 70° C. for 40 hours. After that, the amount of carbon dioxide was determined from the results of the density of the carbon dioxide measured by using a gas detecting tube and the degree of volume expansion in the container. The results are shown in Table 2.

TABLE 2

| | | | | |
|---|---|---|---|---|
| Relative Humidity at Pre-kneading | 40% | 69% | 40% | 69% |
| Relative Humidity at mixing of Chlorosilane-based Molecule | <5% | <5% | 69% | 69% |
| Amount of Carbon Dioxide after Storage at 70° C. | ~0 ml | 0.2 ml | 0.2 ml | 0.4 ml |

In the case where pre-mixing was carried out in an environment having a vapor density of 0.011 kg/m$^3$ or more, which condition was further worse than that of Comparative Example 2, and the pre-mixed molecules not having active hydrogen groups were mixed with chlorosilane-based molecules in an environment having a vapor density of 0.0076 kg/m$^3$ or more, the results obtained were further worth than the results of Comparative Examples 1 and 2.

As shown in Table 1, in the case of mixing chlorosilane-based molecules and molecules not having active hydrogen groups in the environment having a vapor density of 0.0076 kg/m$^3$ or more, it can be found that the deterioration has proceeded compared to the time when the film was manufactured, since the contact angle is 80° or less, which should normally be about 110°. In the case of storing the mixture at a constant temperature, the deterioration further proceeds. In the case where the pre-kneading was carried out in an environment having a vapor density of 0.011 kg/m$^3$ or more, the pre-kneaded material was deteriorated after being stored at a high temperature, even if the mixing with chlorosilane-based molecules was carried out in an environment having a vapor density of 0.0076 kg/m$^3$ or less as a next step. The solution of Example 1 was transparent, but the solution of Comparative Example 1 was cloudy and a lot of white suspended matter was observed in the solution. The comparison of the state in Example 2 and in Comparative Example 2 by visual observations was not possible as in Example 1 and in Comparative Example 1, since a white hydrocarbon compound has been kneaded in Example 2 and in Comparative Example 2.

As shown in Table 2, in the case where the pre-kneading was carried out in an environment having a vapor density of 0.011 kg/m$^3$ or more and in the case where the mixing of the chlorosilane-based molecules and the pre-kneaded material mentioned above was carried out in an environment having a vapor density of 0.0076 kg/m³ or more, the most carbon dioxide was generated when both were handled under high humidity, and the generation of carbon dioxide was observed also when any one of them was handled under high humidity. However, the generation of carbon dioxide was not observed when the both manipulations were handled while controlling the humidity below a specified value. Thus, it was confirmed that controlling humidity is very important for the method for manufacturing the chemically bonding material and the chemically bonding material according to the present invention.

Moreover, the same results can be obtained also using other halosilane-based molecules having high reactivity instead of using chlorosilane-based molecules. Since alkoxysilane-based molecules become silanol-based molecules having high reactivity due to the presence of water molecules, the reaction among molecules occurs, which hinder the formation of a coating film. Accordingly, the same results as in the Examples and in the Comparative Examples mentioned herein are obtained. The same results as mentioned above can be obtained also in the case of using germanium-based, tin-based, titanium-based or zirconium-based molecules, which have an equivalent activity to or more activity than silicon-based molecules.

Furthermore, the state of forming a coating film in the Examples and in the Comparative Examples was judged by measuring the contact angles. The judgement enables the density of the tricarbonfluoride group and the exposure of dicarbonfluoride other than tricarbonfluoride, which is inferior in water repelling, to be detected by differences in the density and in the orientation of the molecules, since the tricarbonfluoride group of the chlorosilane-based molecules used is exposed on the surface of the coating film. Thus, the state of a coating film can be detected easily by measuring a contact angle. The results obtained herein can apply to chlorosilane-based molecules composed only of hydrocarbon groups not having carbonfluoride groups.

As described above, the present invention enables a thin coating film having a high molecular density for forming a film and uniformity in thickness to be formed, which was not possible in a conventional technique, by the following steps: producing a chemically bonding material for forming a thin coating film whose thickness is less than a micrometer and is uniform without deactivating; preparing the material into a coating solution composition; and storing it.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A method for manufacturing a chemically bonding material comprising the steps of: mixing a compound expressed by a general formula $ABX_n$ (Formula 1), wherein A is a group including carbon, B indicates Si, Ge, Sn, Ti or Zr, X is a hydrolyzable group and n indicates 1, 2 or 3, and at least one kind of compound not including active hydrogen groups in a dry atmosphere having a water vapor density of 0.0076 kg/m³ or less; and storing the same in a dry atmosphere having a water vapor density of 0.0076 kg/m³ or less.

2. A method for manufacturing a chemically bonding material according to claim 1, wherein X is at least one group selected from a halogen group and an alkoxy group.

3. A method for manufacturing a chemically bonding material according to claim 1, wherein the compound not including active hydrogen groups is stored in an atmosphere having a water vapor density of 0.0076 kg/m³ or less before being mixed with the compound expressed by the general formula (Formula 1) in an atmosphere having a water vapor density of 0.0076 kg/m³ or less.

4. A method for manufacturing a chemically bonding material according to claim 1, wherein a further material added, other than a compound expressed by the general formula (Formula 1) and a compound not including active hydrogen groups which are included in the chemically bonding material, is also stored in an atmosphere having a water vapor density of 0.0076 kg/m³ or less before being mixed with the compound expressed by the general formula (Formula 1) in an atmosphere having a water vapor density of 0.0076 kg/m³ or less.

5. A method for manufacturing a chemically bonding material according to claim 4, wherein the further material added is an inorganic substance for desiccating a solution.

6. A method for manufacturing a chemically bonding material according to claim 5, wherein the inorganic substance is at least one material selected from an inorganic oxide and a mineral salt.

7. A method for manufacturing a chemically bonding material according to claim 1, wherein the compound not including active hydrogen groups is at least one compound selected from a non proton-based compound, a hydrocarbon compound, a siloxane compound, carbon tetrachloride, chloroform and dichloroethane.

8. A method for manufacturing a chemically bonding material according to claim 1, wherein a compound expressed by the general formula (Formula 1) is stored in an atmosphere having a water vapor density of 0.0076 kg/m³ or less before being mixed with the compound not including active hydrogen groups in an atmosphere having a water vapor density of 0.0076 kg/m³ or less.

9. A method for manufacturing a chemically bonding material according to claim 1, wherein the compound expressed by the general formula $ABX_n$ (Formula 1) is at least one compound expressed by the following (1)–(11):

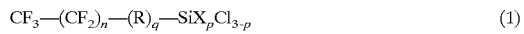 (1)

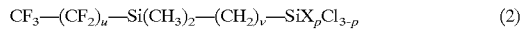 (2)

 (3)

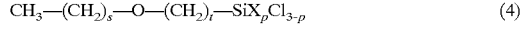 (4)

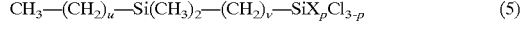 (5)

 (6)

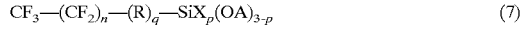 (7)

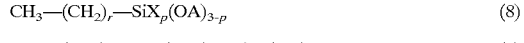 (8)

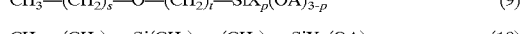 (9)

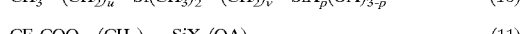 (10)

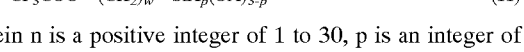 (11)

wherein n is a positive integer of 1 to 30, p is an integer of 0 to 2, q is 0 or 1, r is an integer of 1 to 25, s is an integer of 0 to 12, t is an integer of 1 to 20, u is an integer of 0 to 12, v is an integer of 1 to 20, and w is an integer of 1 to 25, R is an alkyl group, a vinyl group, an ethynyl group, an aryl group, silicon or substituent containing an oxygen atom, and X is hydrogen, an alkyl group, an alkoxyl group, a fluorine containing alkyl group, or a fluorine containing alkoxyl group.

10. A method for manufacturing a chemically bonding material composed of a compound expressed by a general formula $ABX_n$ (Formula 1), wherein A indicates a group including carbon, B indicates Si, Ge, Sn, Ti or Zr, X is a hydrolyzable group and n indicates 1, 2 or 3, and at least two kinds of compounds not including active hydrogen groups, wherein at least the two kinds of compounds not including active hydrogen groups are pre-mixed in an atmosphere having a water vapor density of 0.011 kg/m³ or less, and the mixture composed of the compound expressed by the general formula (Formula 1) and at least the two kinds of compounds not including active hydrogen groups is further prepared and stored in an atmosphere having a water vapor density of 0.0076 kg/m³ or less.

11. A method for manufacturing a chemically bonding material according to claim 10, wherein the at least two kinds of compounds not including active hydrogen groups are stored in an atmosphere having a water vapor density of 0.0076 kg/m³ or less before being mixed with the compound expressed by the general formula (Formula 1) in an atmosphere having a water vapor density of 0.011 kg/m³ or less.

12. A method for manufacturing a chemically bonding material according to claim 10, wherein a further material added, other than a compound expressed by the general formula (Formula 1) and a compound not including active hydrogen groups which are included in the chemically bonding material, is also stored in an atmosphere having a water vapor density of 0.0076 kg/m³ or less before being mixed with the compound expressed by the general formula (Formula 1) in an atmosphere having a water vapor density of 0.0076 kg/m³ or less.

13. A method for manufacturing a chemically bonding material according to claim 12, wherein the further material added is an inorganic substance for desiccating a solution.

14. A method for manufacturing a chemically bonding material according to claim 13, wherein the inorganic substance is at least one material selected from an inorganic oxide and a mineral salt.

15. A method for manufacturing a chemically bonding material according to claim 10, wherein the compound not including active hydrogen groups is at least one compound selected from a non proton-based compound, a hydrocarbon compound, a siloxane compound, carbon tetrachloride, chloroform and dichloroethane.

16. A method for manufacturing a chemically bonding material according to claim 10, wherein the compound expressed by the general formula (Formula 1) is stored in an atmosphere having a water vapor density of 0.0076 kg/m³ or less before being mixed with the compound not including active hydrogen groups in an atmosphere having a water vapor density of 0.0076 kg/m³ or less.

17. A method for manufacturing a chemically bonding material according to claim 10, wherein the compound expressed by the general formula $ABX_n$ (Formula 1) is at least one compound expressed by the following (1)–(11):

$$CF_3-(CF_2)_n-(R)_q-SiX_pCl_{3-p} \quad (1)$$

$$CF_3-(CF_2)_u-Si(CH_3)_2-(CH_2)_v-SiX_pCl_{3-p} \quad (2)$$

$$CH_3-(CH_2)_r-SiX_pCl_{3-p} \quad (3)$$

$$CH_3-(CH_2)_s-O-(CH_2)_t-SiX_pCl_{3-p} \quad (4)$$

$$CH_3-(CH_2)_u-Si(CH_3)_2-(CH_2)_v-SiX_pCl_{3-p} \quad (5)$$

$$CF_3COO-(CH_2)_w-SiX_pCl_{3-p} \quad (6)$$

$$CF_3-(CF_2)_n-(R)_q-SiX_p(OA)_{3-p} \quad (7)$$

$$CH_3-(CH_2)_r-SiX_p(OA)_{3-p} \quad (8)$$

$$CH_3-(CH_2)_s-O-(CH_2)_t-SiX_p(OA)_{3-p} \quad (9)$$

$$CH_3-(CH_2)_u-Si(CH_3)_2-(CH_2)_v-SiX_p(OA)_{3-p} \quad (10)$$

$$CF_3COO-(CH_2)_w-SiX_p(OA)_{3-p} \quad (11)$$

wherein n is a positive integer of 1 to 30, p is an integer of 0 to 2, q is 0 or 1, r is an integer of 1 to 25, s is an integer of 0 to 12, t is an integer of 1 to 20, u is an integer of 0 to 12, v is an integer of 1 to 20, and w is an integer of 1 to 25, R is an alkyl group, a vinyl group, an ethynyl group, an aryl group, silicon or substituent containing an oxygen atom, and X is hydrogen, an alkyl group, an alkoxyl group, a fluorine containing alkyl group, or a fluorine containing alkoxyl group.

18. A chemically bonding material comprising having stored a compound expressed by a general formula $ABX_n$ (Formula 1), wherein A indicates a group including carbon, B indicates Si, Ge, Sn, Ti or Zr, X is a hydrolyzable group and n indicates 1, 2 or 3, and at least one kind of compound not including active hydrogen groups in an atmosphere having a water vapor density of 0.0076 kg/m³ or less.

19. A chemically bonding material according to claim 18, wherein the compound not including active hydrogen groups is at least one compound selected from a non proton-based compound, a hydrocarbon compound, a siloxane compound, carbon tetrachloride, chloroform and dichloroethane.

20. A chemically bonding material according to claim 19, wherein a further material added that is an inorganic substance for desiccating a solution.

21. A chemically bonding material according to claim 20, wherein the inorganic substance is at least one material selected from an inorganic oxide and a mineral salt.

22. A chemically bonding material according to claim 18, wherein a composition comprising a compound expressed by a general formula (Formula 1) and at least one kind of compound not having active hydrogen groups are stored in a hermetically sealed enclosure in an atmosphere having a water vapor density of 0.0076 kg/m³ or less.

23. A chemically bonding material according to claim 22, wherein the hermetically sealed enclosure is at least one enclosure selected from a tube, a canister, a bottle and a capsule.

24. A chemically bonding material according to claim 18, wherein the compound expressed by the general formula $ABX_n$ (Formula 1) is at least one compound expressed by the following (1)–(11):

$$CF_3-(CF_2)_n-(R)_q-SiX_pCl_{3-p} \quad (1)$$

$$CF_3-(CF_2)_u-Si(CH_3)_2-(CH_2)_v-SiX_pCl_{3-p} \quad (2)$$

$$CH_3-(CH_2)_r-SiX_pCl_{3-p} \quad (3)$$

$$CH_3-(CH_2)_s-O-(CH_2)_t-SiX_pCl_{3-p} \quad (4)$$

$$CH_3-(CH_2)_u-Si(CH_3)_2-(CH_2)_v-SiX_pCl_{3-p} \quad (5)$$

$$CF_3COO-(CH_2)_w-SiX_pCl_{3-p} \quad (6)$$

$$CF_3-(CF_2)_n-(R)_q-SiX_p(OA)_{3-p} \quad (7)$$

$$CH_3-(CH_2)_r SiX_p(OA)_{3-p} \quad (8)$$

$$CH_3-(CH_2)_s-O-(CH_2)_t-SiX_p(OA)_{3-p} \quad (9)$$

$$CH_3-(CH_2)_u-Si(CH_3)_2-(CH_2)_v-SiX_p(OA)_{3-p} \quad (10)$$

$$CF_3COO-(CH_2)_w-SiX_p(OA)_{3-p} \quad (11)$$

wherein n is a positive integer of 1 to 30, p is an integer of 0 to 2, q is 0 or 1, r is an integer of 1 to 25, s is an integer of 0 to 12, t is an integer of 1 to 20, u is an integer of 0 to 12, v is an integer of 1 to 20, and w is an integer of 1 to 25, R is an alkyl group, a vinyl group, an ethynyl group, an aryl group, silicon or substituent containing an oxygen atom, and X is hydrogen, an alkyl group, an alkoxyl group, a fluorine containing alkyl group, or a fluorine containing alkoxyl group.

* * * * *